United States Patent [19]

Sakaguchi et al.

[11] Patent Number: 5,157,004
[45] Date of Patent: Oct. 20, 1992

[54] POLYPEPTIDES AND PRODUCTION THEREOF

[75] Inventors: Masao Sakaguchi, Ikeda; Susumu Honda, Nishinomiya; Osamu Nishimura, Kawanishi, all of Japan

[73] Assignee: Takeda Chemical Industries, Ltd., Osaka, Japan

[21] Appl. No.: 575,552

[22] Filed: Aug. 29, 1990

Related U.S. Application Data

[62] Division of Ser. No. 136,712, Dec. 22, 1987, Pat. No. 4,980,455.

[30] Foreign Application Priority Data

Dec. 27, 1986 [JP] Japan .................. 60-313382
Sep. 11, 1987 [JP] Japan .................. 61-229317

[51] Int. Cl.[5] .................. C12N 15/00; C12N 15/19; C12N 15/70
[52] U.S. Cl. .................. 435/240.2; 435/69.51; 435/252.3; 435/252.33; 435/325.1; 536/27; 935/10
[58] Field of Search ............ 435/240.1, 252.3, 252.35, 435/320.1, 172.3, 69.1, 69.51; 536/27; 935/10, 11, 13

[56] References Cited

U.S. PATENT DOCUMENTS 4,832,959 5/1989 Engles .................. 424/85.5
4,855,238 8/1989 Gray et al. .................. 435/172.3

FOREIGN PATENT DOCUMENTS 0146354 6/1985 European Pat. Off. .
0166993 1/1986 European Pat. Off. .
1793619 8/1972 France .
3536939 4/1987 France .

OTHER PUBLICATIONS

Gray et al., Nature 298: 859 (1982).
Capon et al., in the Third Annual International Congress for Interferon Research, Miami, Fla., Abstract (1982).
Roberts et al., Proc. Natl. Acad. Sci. USA 76: 760 (1979).

*Primary Examiner*—James Martinell
*Attorney, Agent, or Firm*—David G. Conlin; Ronald I. Eisenstein

[57] ABSTRACT

The present invention provides a novel polypeptide which shows higher IFN-γ activity than intact IFN-γ and a method of producing the same.

The polypeptides not only possesses a remarkable antiviral activity, antitumor activity, immunopotentiating activity etc. but also is highly stable, therefore, it can be used advantageously as pharmaceuticals etc.

4 Claims, 4 Drawing Sheets

```
             120              125      146 ...
    ... GTG ATG GCT GAA CTG TCG CCA ... CAG TAA TGGTTGTCCTGC ...

123        ...
    a) ATG GCT GAA CTG  —  TAA TGG TTG TCC

124            ...
    b) GCT GAA CTG TCG  —  TAA TGG TTG TCC

125            ...
    c) GAA CTG TCG CCA  —  TAA TGG TTG TCC
```

```
1
Cys Tyr Cys Gln Asp Pro Tyr Val Lys Glu Ala Glu Asn
                              20
Leu Lys Lys Tyr Phe Asn Ala Gly His Ser Asp Val Ala

Asp Asn Gly Thr Leu Phe Leu Gly Ile Leu Lys Asn Trp
40
Lys Glu Glu Ser Asp Arg Lys Ile Met Gln Ser Gln Ile
                              60
Val Ser Phe Tyr Phe Lys Leu Phe Lys Asn Phe Lys Asp

Asp Gln Ser Ile Gln Lys Ser Val Glu Thr Ile Lys Glu
    80
Asp Met Asn Val Lys Phe Phe Asn Ser Asn Lys Lys Lys
                                  100
Arg Asp Asp Phe Glu Lys Leu Thr Asn Tyr Ser Val Thr

Asp Leu Asn Val Gln Arg Lys Ala Ile His Glu Leu Ile
        120
Gln Val Met Ala Glu Leu Ser Pro Ala Ala Lys Thr Gly
                                      140
Lys Arg Lys Arg Ser Gln Met Leu Phe Arg Gly Arg Arg
        146
Ala Ser Gln
```

FIG. 4

POLYPEPTIDES AND PRODUCTION THEREOF

This is a divisional of application Ser. No. 07/136,712 filed on Dec. 22, 1987, now U.S. Pat. No. 4,980,455.

BACKGROUND OF THE INVENTION

Field of the Invention

The present invention relates to novel polypeptides which are useful as pharmaceuticals etc. and production thereof.

γ-interferon (hereinafter also referred to as IFN-γ) is produced by immunocompetent cells under the same condition as those promoting lymphocyte blastogenesis and lymphokine production, thus it is also named immune interferon. IFN-γ is reported to be higher in cell proliferation inhibitory activity and antitumor activity than IFN-α and IFN-β; it is expected that this type of interferon will work well in clinical application. At present, however, there is no efficient process for its production because these are some drawbacks involved, e.g., its production requires the supply of fresh lymphocytes.

As a result of the application of gene recombination technology, however, the nucleotide sequence and amino acid sequence (deduced from the former) of the complementary DNA (cDNA) of IFN-γ have recently been clarified by cloning the cDNA; it has also become possible to make cDNA and chemically synthesized genes express themselves using various host species [Gray, P. W. et al., Nature, 295, 503 (1982); Debos, R. et al., Nucleic Acids Research, 10, 2487 (1982); Tanaka, S. et al., Nucleic Acids Research, 11, 1707 (1983)].

Gray et al. [Nature, 295, 503 (1982)] and Derynck et al. [Nucleic Acids Research, 10, 3605 (1982)] refer to a peptide composed of 146 amino acid molecules as IFN-γ. The same amino acid numbers as those in the above-mentioned references are used in the present specification (refer to FIG. 4).

It has also become possible to mass-produce IFN-γ obtained via gene recombination (hereinafter also referred to as rIFN-γ) using monoclonal antibodies [EP Patent Publication No. 0103898].

Many attempts have been made to delete, from the amino acid sequence of IFN-γ, partial amino acid sequences which are not thought to be directly related to the bioactivity of IFN-γ.

For example, Japanese Patent Laid-open No. 202899/1985 which corresponds to EPC Patent Publication No. 146354 discloses amino acid sequences resulting from either the deletion of the N-terminal peptide chain

```
    1   2   3
   Cys—Tyr—Cys
``` in IFN-γ or the deletion of an amino acid sequence of peptide composed of 1 to 17 amino acid molecules starting from the C-terminal in the C-terminal peptide chain

```
   130         146
   Gly— ... —Gln
``` of IFN-γ.

In addition, Japanese Patent Laid-open No. 233100/1985 which corresponds to EP Patent Publication No. 161504 discloses partial amino acid sequences of IFN-γ: 5 to 127, 1 to 127 and 5 to 146. Of the three, however, the amino acid sequence 5 to 127 does not express itself as a polypeptide, though the DNA for peptide expression is constructed.

Japanese Patent Laid-open No. 5096/1986 which corresponds to EP Patent Publication No. 166993 discloses amino acid sequences resulting from the deletion of the N-terminal amino acid sequence Cys-Tyr, Cys-Tyr-Cys or Cys-Tyr-Cys-Gln in IFN-γ and the deletion of an amino acid sequence or a peptide composed of 1 to 16 amino acid molecules starting from the C-terminal in the C-terminal peptide chain

```
   131         146
   Lys— ... —Gln
``` of IFN-γ.

SUMMARY OF THE INVENTION

As described above, investigations have been made on polypeptides resulting from the deletion of N-terminal or C-terminal amino acid sequence or peptide in IFN-γ. The purpose of the present invention is to provide a polypeptide having high IFN-γ activity whose C-terminal amino acid sequence is shorter than that of any of the above mentioned polypeptides.

Figure 4:
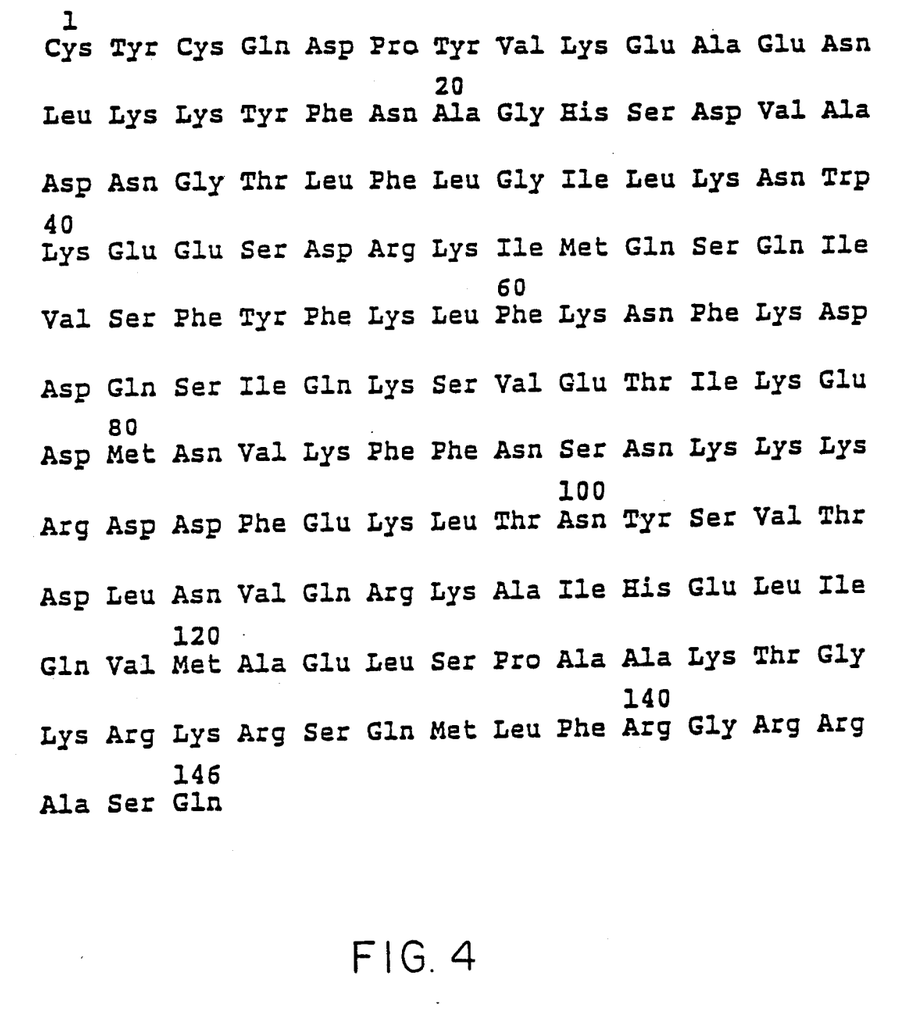
FIG. 4 shows the amino acid sequence of IFN-γ and the number of the amino acid used in the present specification.

After research to determine the active site of rIFN-γ, the present inventors found that partial polypeptides of IFN-γ which are shorter than the partial polypeptide whose C-terminal amino acid is the Ala at the 126th position and whose C-terminal amino acid is the amino acid from the Glu at the 122nd position to the Pro at the 125th position show higher IFN-γ activity than the intact IFN-γ shown in FIG. 4.

The present inventors made further investigations based on this finding to develop the present invention.

The present invention involves:

(1) Polypeptide (I) of the formula (I):

[Wherein, X represents Met or a chemical bond; Y represents Gln or a chemical bond when X represents Met, and Y represents Gln, <Glu or a chemical bond when X represents a chemical bond; Z represents an amino acid or a peptide composed of 1 to 4 amino acid molecules starting from the N-terminal in the peptide chain (N) Glu Leu Ser Pro (C).]

(2) A DNA which segment comprises a region of nucleotides encoding Polypeptide (I).

(3) A transformant which carries the DNA segment as defined in paragraph (2).

(4) A method for producing Polypeptide (I), which comprises cultivating the transformant as defined in paragraph (3) in a culture medium to produce and accumulate Polypeptide (I) in a culture, and then collecting Polypeptide (I).

BRIEF DESCRIPTION OF THE DRAWINGS

FIGS. 1-1 to 1-2 shows the construction chart of the plasmid pIGT-123 disclosed in Example 1 (→ represents an IFN-γ gene; represents mutation sites).

DETAILED DESCRIPTION

Any DNA segment can be used for the present invention, as long as it has a region of nucleotides encoding Polypeptide (I).

Examples of such DNA segments include segments of the formula (II):

```
(5') Y'—GAC CCA TAT GTA AAA GAA GCA        (II)
GAA AAC CTT AAG AAA TAT TTT AAT GCA
GGT CAT TCA GAT GTA GCG GAT AAT GGA
ACT CTT TTC TTA GGC ATT TTG AAG AAT
TGG AAA GAG GAG AGT GAC AGA AAA ATA
ATG CAG AGC CAA ATT GTC TCC TTT TAC
TTC AAA CTT TTT AAA AAC TTT AAA GAT
GAC CAG AGC ATC CAA AAG AGT GTG GAG
ACC ATC AAG GAA GAC ATG AAT GTC AAG
TTT TTC AAT AGC AAC AAA AAG AAA CGA
GAT GAC TTC GAA AAG CTG ACT AAT TAT
TCG GTA ACT GAC TTG AAT GTC CAA CGC
AAA GCA ATA CAT GAA CTC ATC CAA GTG
ATG GCT—Z'(3')
```

[Wherein Y' represents CAG or a chemical bond; Z' represents a base sequence composed of 1 to 4 codons starting from the 5'-terminal in the base sequence (5') GAA CTG TCG CCA (3').]

A DNA segment of the present invention may be a plasmid containing a region encoding Polypeptide (I) as well as a DNA segment itself encoding Polypeptide (I).

DNA segment having ATG at 5'-terminal, a region encoding Polypeptide (I) downstream of the said codon and a terminator codon can be produced by methods well known in the art, including processing either the cDNA of published IFN-γ obtained via chemical synthesis or gene engineering, or chromosome-derived IFN-γ DNA or chemically synthesizing a segment based upon the present disclosure.

As examples of plasmids which can be used as vectors for the production of DNA segments capable of encoding Polypeptide (I), mention may be made of ColEI-derived plasmids pBR322 [Gene, 2, 95 (1977)], pBR313 [Gene, 2, 75 (1977)], pBR324, pBR325 [Gene, 4, 121 (1978)], pBR327, pBR328 [Gene, 9, 287 (1980)], pKY2289 [Gene, 3, 1 (1978)], pKY2700 [Seikagaku, 52, 770 (1980)], pACYC177, pACYC184 [Journal of Bacteriology, 134, 1141 (1978)], pRK248, pRK646, pDF [Methods in Enzymology, 68, 268 (1979)], pUC18 and pUC19 [Janisch-Peron et al.; Gene, 33, 103 (1985)]. It is also possible to use bacteriophage-derived plasmids: vectors using phage such as λgt.λc [Proc. Natl. Acad. Sci. USA, 71, 4579 (1974)], λgt.λB [Proc. Natl. Acad. Sci. USA, 72, 3416 (1975)] and λDam [Gene, 1, 255 (1977)]; Charon vector [Science, 196, 161 (1977); Journal of Virology, 29, 555 (1979)]; and vectors using filamentous phage such as mp18 and mp19 [Janisch-Peron et al.; Gene, 33, 103 (1985)].

It is preferable that said DNA have a promoter upstream of the codon ATG; any promoter can be used, as long as it is suitable for the species used as host for transformant production.

Examples of such promoters include trp promoter, lac promoter, rec A promoter, λPL promoter and lpp promoter, for Escherichia coli; SPO1 promoter, SPO2 promoter and penP promoter, for Bacillus subtilis; PHO5 promoter, PGK promoter, GAP promoter and ADH promoter, for yeast (Saccharomyces cerevisiae); and SV40-derived promoter, for animal cells.

As an example of the application of the above-mentioned production method, mention is hereinafter made of the method of producing a plasmid containing a DNA segment having a region encoding Polypeptide (I) wherein Z represents the peptide Gln-Leu using as a starting material the plasmid pLC2, which contains the IFN-γ gene (cDNA) (refer to Reference Example 4, EP Patent Publication No. 154316).

A DNA fragment encoding the entire region of IFN-γ can be obtained by digesting the plasmid pLC2 using a restriction enzyme, e.g. EcoRI. This fragment is integrated into the M13 phage-derived vector mp19 to obtain a single-stranded phage DNA sequence containing the IFN-γ gene.

This single-stranded DNA sequence and the oligonucleotide ATG GCT GAA CTG TAA TGG TTG TCC synthesized using, for example, the phosphamidite method are then used in combination to obtain the above-mentioned IFN-γ-encoding DNA fragment wherein the codon from the 124th to the 146th position is deleted by, for example, the conventional site-specific mutagenesis method using, for instance, a kit of Amersham International plc, Buckinghamshire, England [oligonucleotide-directed in vitro mutagenesis system]. The resulting DNA fragment is linked to an appropriate promoter at the downstream side and then introduced to an appropriate host; in certain instances it is preferable to insert an SD (Shine-Dalgarno) sequence downstream of the promotor.

The transformant of the present invention can be produced by transforming the host with an expression plasmid obtained as above using a per se conventional method [Cohen, S. N. et al.: Proc. Natl. Acad. Sci. U.S.A., 69, 2110 (1972)].

Escherichia bacteria, Bacillus bacteria, yeasts, etc. may be used as hosts for microorganisms to be transformed.

Types of Escherichia bacteria which can be used include Escherichia coli, specifically Escherichia coli strains K12DH1 [Proc. Natl. Acad. Sci. U.S.A., 60, 160 (1968)], JM-103 [Nucleic Acids Research, 9, 309 (1981)], JA221 [Journal of Molecular Biology 120, 517 (1978)], HB101 [Journal of Molecular Biology, 41, 459 (1969)], C600 (Genetics, 39, 440 (1954)], N4830 [Cell, 25, 713 (1981)] and K-12MM294 [Proc. Natl. Acad. Sci. U.S.A., 73, 4174 (1976)].

Types of Bacillus bacteria which can be used include Bacillus subtilis, specifically Bacillus subtilis strains MI114 [Gene, 24, 255 (1983)] and 207-21 [Journal of Biochemistry, 95, 87 (1984)].

Yeasts which can be used include *Saccharomyces cerevisiae*, specifically *Saccharomyces cerevisiae* strains AH22 [Proc. Natl. Acad. Sci. U.S.A., 75, 1929 (1978)], XSB52-23C [Proc. Natl. Acad. Sci. U.S.A., 77, 2173 (1980)], BH-641A (ATCC 28339), 20B-12 [Genetics, 85, 23 (1976)] and GM3C-2 [Proc. Natl. Acad. Sci. U.S.A., 78, 2258 (1981)].

Animal cells which can be used include simian cell COS-7 [Cell, 23, 175 (1981)], Vero [Nihon-Rinsho, 21, 1209 (1963)], Chinese hamster cell CHO [J. Exp. Med., 108, 945 (1985)], murine L-cells [J. Nat. Cancer Inst., 4, 165 (1943)], human FL-cells [Proc. Soc. Exp. Biol. Med., 94, 532 (1957)] and hamster C-cells.

Polypeptide (I) can be produced by cultivating the above-metnioned transformant to produce and accumulate Polypeptide (I) in a culture and then collecting Polypeptide (I).

Examples of culture media which can be used, include M9 medium, which contains glucose and casamino acid, [Miller, J.; Experiments in Molecular Genetics, 431–433, Cold Spring Harbor Laboratory, N.Y., 1972] and 2 x YT medium [Messing; Methods in Enzymology, 101, 20 (1983)]. Agents such as $3\beta$-indolylacrylic acid can be added to increase promoter efficiency, if necessary.

Culturing should be carried out at 15° to 43° C. for 3 to 24 hours; with aerating and/or stirring, if necessary.

When a transformant having both a λcIts repressor and an expression vector containing a PL-promoter is cultured, it is preferable that culturing and repressor inactivation be at 30° to 36° C. and 37° to 42° C., respectively. Chemical agents such as mitomycin C and nalidixic acid may be added to increase recA promoter efficiency, i.e., to decrease recA gene expression suppressing activity, if necessary; ultraviolet irradiation is also possible.

After the completion of culturing, bacterial cells are collected using a conventional method and then treated to obtain a supernatant. For example, after suspending in a buffer solution, the bacterial cells are disintegrated by e.g. protein denaturizer treatment, ultrasonication and enzymatic reaction using lysozyme etc., after which the suspension is subjected to a conventional process such as centrifugation to obtain a supernatant.

It is also possible to produce Polypeptide (I) wherein Z is a polypeptide or amino acid residue composed of 3 or less amino acid molecules by culturing a transformant having a DNA segment containing a region encoding Polypeptide (I) wherein Z is a polypeptide or amino acid residue composed of more amino acid molecules than in the former (e.g. a polypeptide wherein Z is a peptide having all 4 above-mentioned amino acid molecules), after which the resulting culture is purified under conditions facilitating the action of protease in the transformant.

Polypeptide (I) can be separated from the resulting supernatant, using a conventional method of protein purification. Antibodies which are combinable to IFN-γ or Polypeptide (I) work well for this purpose; the use of a column using such antibodies is particularly preferable. As an example of such an antibody column, mention may be made of the monoclonal antibody column for the peptide <Glu-Asp-Pro-Tyr-Val-Lys-Glu-Ala-Glu-Asn-Leu-Lys-Lys-Tyr-Phe-Asn-Ala-Gly-OH [Example 11, Japanese Patent Laid-open No. 107569/1985 and Hybridoma 6 (2), 173 (1987) (antibody column using the monoclonal antibody WNγ2-76.53)].

In a purification method using such an antibody column, the following procedure can be used. The culture containing Polypeptide (I) is dissolved in a nearly neutral buffer solution, e.g. a phosphate buffer solution and a tris HCl buffer solution, after which it is absorbed to the antibody column. After washing the column with the same buffer solution as above, Polypeptide (I) is eluted.

Solutions which can be used as eluents include slightly acidic solutions such as acetic acid solutions, solutions containing polyethylene glycol, solutions containing a peptide which is more likely to combine with antibodies than Polypeptide (I), and high-concentration salt solutions. These can be used either singly or in combination; the use of a solution which is not highly accelerative to the decomposition of Polypeptide (I) is recommended.

The resulting eluate should be neutralized with a buffer solution using a routine method; repeat the procedure described above, if necessary.

Polypeptide (I) may be obtained in the form of a mixture of the polypeptide wherein X is a chemical bond and that wherein X is Met.

Polypeptide (I) wherein Gln is the N-terminal amino acid may also be obtained in the form of a mixture with Polypeptide (I) wherein <Glu is the counterpart. This mixture can be used for the following purpose even without any pretreatment; however, it preferably should be converted to Polypeptide (I) wherein <Glu is the N-terminal amino acid via heat or weak acid (e.g. dilute acetic acid) treatment following the above-mentioned procedure.

Among thus obtained Polypeptide (I), preferred is Polypeptide (I) wherein X is Met and Y is Gln.

As examples of more preferable types of Poly-peptide (I) obtained as above, mention may be made of: the polypeptide (hereinafter also referred to as IFN-γ4-123), the polypeptide (hereinafter also referred to as IFN-γ4-124) and the polypeptide (hereinafter also referred to as IFN-γ4-125) which are obtained by the following Example.

The resulting solution of Polypeptide (I) is then subjected to dialysis; it should be powdered by lyophilization, if necessary. In lyophilization, substances such as sorbitol, mannitol, dextrose, maltose and glycerol can be added as stabilizers.

The type of Polypeptide (I) obtained as above not only possesses IFN-γ activity but also is stable (less likely to dimerize or polymerize) due to the lack of Cys; it will work well as a pharmaceutical etc.

The type of Polypeptide (I) of the present invention can be purified to a specific activity of more than $10^6$ U/mg, determined in viral activity assay tests in which the cell degeneration suppressing activity of vesicular stomatitis virus (VSV) on human amnion-derived WISH cells is determined; it can be used for the same purposes and in the same manner as those with published type of rIFN-γ [Gray, P. W. et al.; see above] and natural-type IFN-γ (=type 2 IFN) [Salvin et al.; J. National Cancer Institute, 55, 1233 (1975)].

The type of Polypeptide (I) of the present invention exhibits antiviral, antitumor, cell proliferation suppressing and immunopotentiating actions and, in addition, it is low in toxicity and non-antigenic.

The type of Polypeptide (I) of the present invention can be therefore used as antiviral agent, antitumor agent, cell proliferation suppressor, immunopotentiator etc. for the prevention/therapeutics of viral diseases, tumors and immune depression diseases in warm-blooded mammals (mice, rats, cats, dogs, sheep, goats, bovines, humans etc.).

The type of Polypeptide (I) of the present invention can be used in combination with conventional physiologically acceptable carriers such as sterile water, human serum albumin (HSA) and physiological saline, and it can be administered non-orally via intravenous or intramuscular injection. Its daily dose should be 2,000 to 2,000,000 unit/kg, preferable 80,000 to 800,000 unit/kg.

Pharmaceuticals containing the type of Polypeptide (I) of the present invention may contain other active components, as long as they are physiologically acceptable, such as salts, diluents, adjuvants, other carriers, buffers, binders, surfactants and preservatives. When the type of Polypeptide (I) of the present invention is used as a non-oral pharmaceutical, it should be prepared in ampule, which should contain either a suspension of Polypeptide (I) in either sterile water or a physiologically acceptable solvent or sterile powdered Polypeptide (I) which can be diluted with a physiologically acceptable diluent before use [usually obtained via the lyophilization of a Polypeptide (I) solution].

When the Polypeptide (I) of the present invention is used as a pharmaceutical it is purified so that it contains a minimal amount of pyrogens and endotoxins. Pharmaceuticals are prepared by conventional techniques using aseptic conditions.

The type of Polypeptide (I) of the present invention not only possesses higher IFN-γ activity (antiviral activity, antitumor activity, immunopotentiating activity, etc.) than intact IFN-γ shown in FIG. 4 but also is highly stable, thus working well as pharmaceuticals etc.

The abbreviations for amino acids, peptides, protective groups, active groups and the like, used in the specification and drawings of the present invention are based either on the abbreviations specified by the IUPAC-IUB Commission on Biochemical Nomenclature or those used commonly in related fields, as shown in Table 1. It should be noted that when there is a possibility of the presence of an optical isomer in amino acids etc., the isomer is an L-form unless otherwise stated.

TABLE 1

| | |
|---|---|
| DNA | Deoxyribonucleic acid |
| A | Adenine |
| T | Thymine |
| G | Guanine |
| C | Cytosine |
| RNA | Ribonucleic acid |
| dATP | Deoxyadenosine triphosphate |
| dTTP | Deoxythymidine triphosphate |
| dGTP | Deoxyguanosine triphosphate |
| dCTP | Deoxycytidine triphosphate |
| ATP | Adenosine triphosphate |

TABLE 1-continued

| | |
|---|---|
| EDTA | Ethylenediaminetetraacetic acid |
| SDS | Sodium dodecylsulfate |
| Gly | Glycine |
| Ala | Alanine |
| Val | Valine |
| Leu | Leucine |
| Ile | Isoleucine |
| Ser | Serine |
| Thr | Threonine |
| Met | Methionine |
| Glu | Glutamic acid |
| Asp | Aspartic acid |
| Lys | Lysine |
| Arg | Arginine |
| His | Histidine |
| Phe | Phenylalanine |
| Tyr | Tyrosine |
| Trp | Tryptophan |
| Pro | Proline |
| Asn | Asparagine |
| Gln | Glutamine |
| <Glu | Pyroglutamic acid |

In the present specification, Polypeptide (I) units are shown in JRU (Japanese Reference Unit); unit determinations were made using the following procedure. In an assay based on the cell degeneration suppressing activity of Sindbis Virus on human amnion-derived FL-cells, determinations were made of the cell degeneration suppressing activities of the test sample and a standard sample of known unit (Japan Standard); the antiviral activity (U/ml) of the test sample was then calculated from the relative value obtained above. The specific activity (U/mg) of the test sample is calculated on the basis of its protein concentration (mg/ml).

It should be noted that one unit in JRU is equivalent to 1/6.4 unit as defined in Japanese Patent Laid-open No. 186995/1985 (corresponding to EP Patent Publication No. 110044).

The transformants disclosed in the following Examples, *Escherichia coli* DH1/pRK248cIts/pIGT-123, *Escherichia coli* DH1/pRK248cIts/pIGT-124 and *Escherichia coli* DH1/pRK248cIts/pIGT-125, have been deposited at the Institute for Fermentation, Osaka (IFO), Japan under the accession numbers of IFO 14647, IFO 14648 and IFO 14649 since Sep. 1, 1987, respectively. They have also been deposited at the Fermentation Research Institute, Agency of Industrial Science and Technology, Ministry of International Trade and Industry (FRI), Japan under the accession numbers of FERM BP-1474, FERM BP-1475 and FERM BP-1476 since Sep. 9, 1987, respectively.

The transformant disclosed in the following Reference Examples, *Escherichia coli* N4830/pIGT-126, has been deposited at the IFO under the accession number of IFO 14557 since Dec. 19, 1986. It has also been deposited at the FRI under the accession number of FERM P-9113 since Dec. 25, 1986.

EXAMPLES

The present invention is hereinafter described more explicitly with some examples of its preferred embodiments. It should be noted, however, that the present invention is not confined to these examples.

EXAMPLE 1

(production of transformant)

The IFN-γ expression plasmid pLC2 (refer to Reference Example 4, EP Patent Publication No. 154316)

was digested using the restriction enzyme EcoRI to separate a DNA fragment containing the IFN-γ gene site. This fragment was then integrated to the EcoRI-digested M-13 phage-derived DNA mp19, using T4-DNA ligase, after which it was transduced to *Escherichia coli* strain JM103 [Messing et al.; Nucleic Acids Research, 9, 309 (1981)]. Out of the resulting M-13 phage plaques, those of phage particles containing a minus chain of the IFN-γ gene are selected. DNA was then extracted from the phage particles and purified to obtain the single-stranded DNA mp19-IGT(−).

Figure 2:
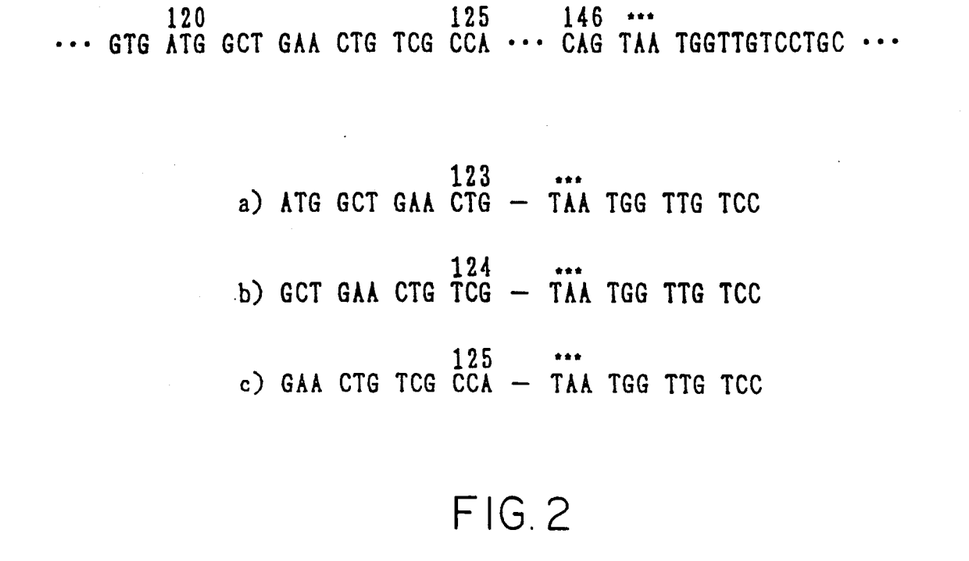
FIG. 2 shows a part of the base sequence of the single-stranded DNA mp19-IGT(−) and synthesized oligonucleotide used in Example 1 (— represents deletion; *** represents termination codon).

This single-stranded DNA and the oligonucleotides (a)-(c) synthesized using the amidite phosphate method: (a) ATGGCTGAACTGTAATGGTTGTCC, (b) GCTGAACTGTCGTAATGG TTGTCC or (c) GAACTGTCGCCATAATGGTTGTTC were then used in combination to induce site-specific mutation by conventional methods using a kit of Amersham International plc, Buckinghamshire, England [oligonucleotide-directed in vitro mutagenesis system]. The above-mentioned oligonucleotides (a)-(c) were respectively designed to delete unnecessary codons of IFN-γ gene and to obtain IFN-γ-encoding DNA segments up to the 123rd[(a)], the 124th[(b)] and the 125th[(c)] position (see FIG. 2).

After DNA manipulation according to the indication of the above-mentioned kit, the plaques was obtained from the *Escherichia coli* JM-103 transformed with the resulting DNA segments and the phage out of the plaques was cultivated using *Escherichia coli* JM-103 as a host. The single-stranded DNA sequence was obtained from phage particles in the culture supernatant and the double-stranded DNA segment was obtained from the host bacterial cell. Base sequences in the mutation site were decided using this single-stranded DNA sequence to confirm the mutation, respectively.

Figure 11:
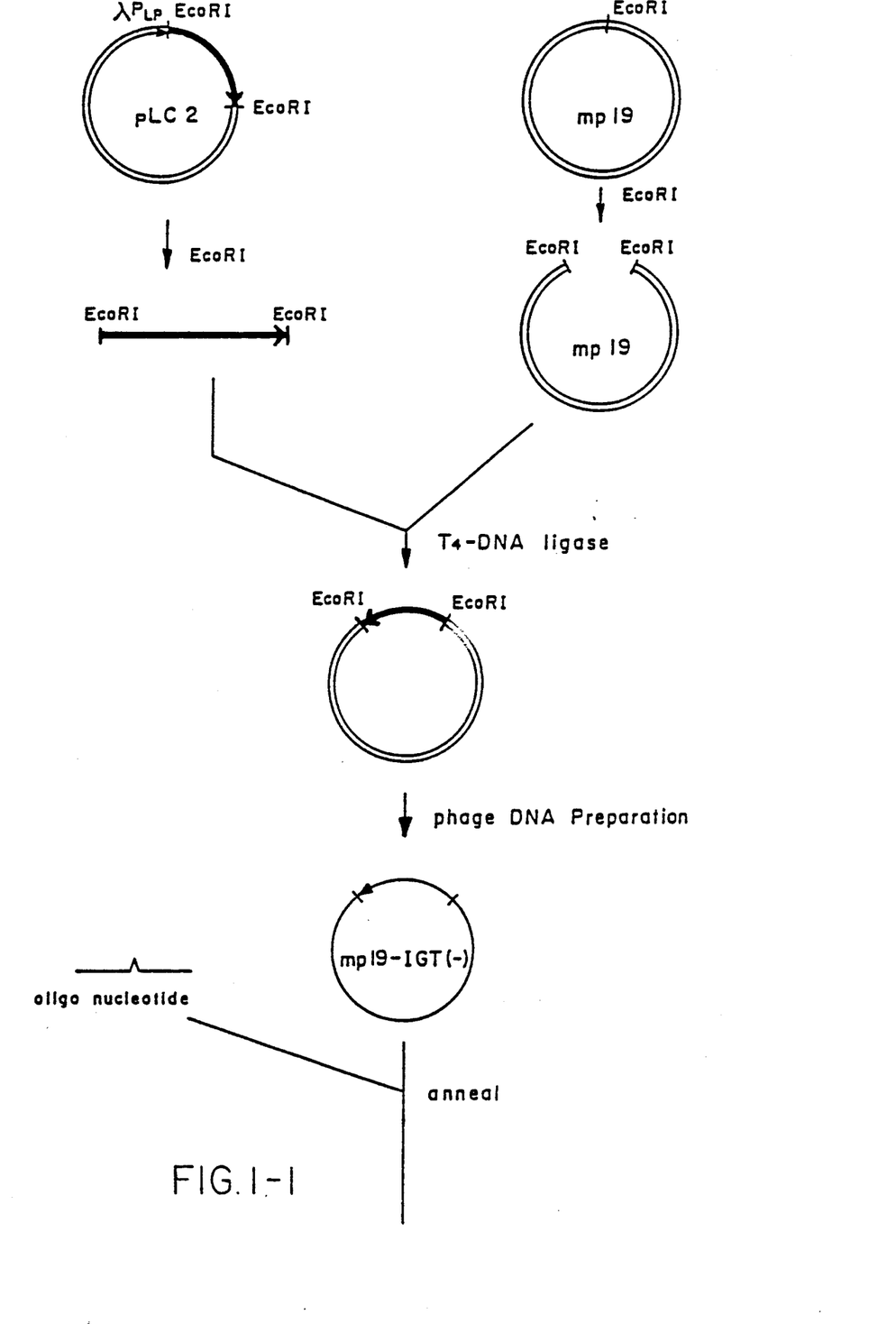
Figure 12:
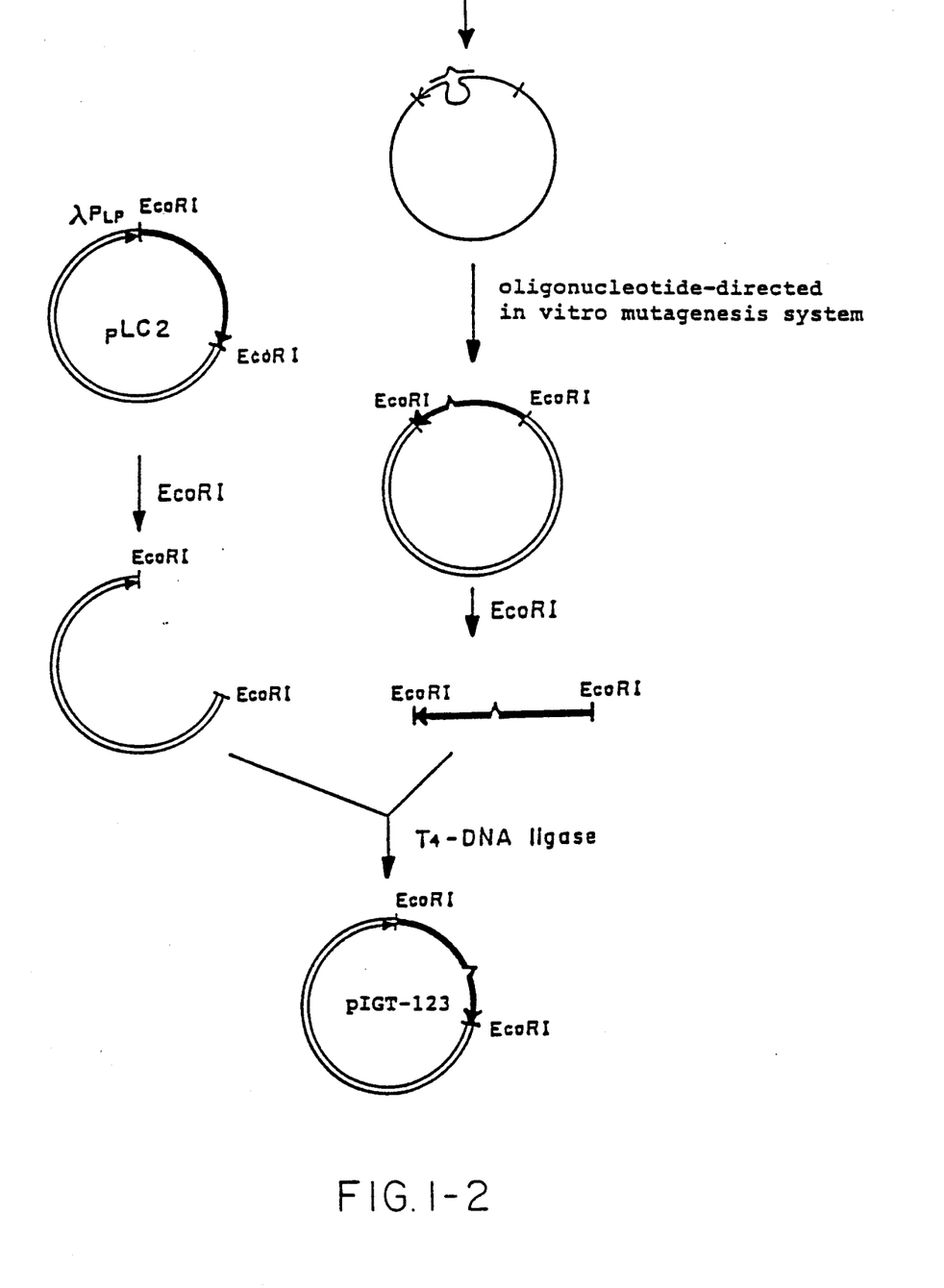

The resulting double-stranded DNA segments were respectively digested using the restriction enzyme EcoRI to separate a DNA fragment of variant IFN-γ gene, which was then inserted downstream of the λPL promoter in the plasmid pLC2, previously digested using the restriction enzyme EcoRI (see FIG. 1). Separately, *Escherichia coli* strain DH1 was transformed using the plasmid pRK248cIts [Hansurich et al.; Methods in Enzymology, 68, 482 (1979)], which has a temperature-sensitive repressor gene of PL promoter, in accordance with the protocol of Maniatis et al. [Molecular Cloning, pp250-251, Cold Spring Harbor Laboratory 1982)] to establish the strain *E. coli* DH1/pRK248cIts. This strain was further transformed using the above-mentioned DNA in the same manner as above and the transformant *Escherichia coli* DH1/pRK248cIts/pIGT-123 (IFO 14647, FERM BP-1474) having the expression plasmid pIGT-123, which encodes the polypeptide

```
   1   2   3   124
[des—Cys—Tyr—Cys,des—Ser— ... —
                         146
                         Gln]IFN-γ (IFN-γ 4-123),
``` the transformant *Escherichia coli* DH1/pRK248cIts/pIGT-124 (IFO 14648, FERM BP-1475) having the expression plasmid pIGT-124, which encodes the polypeptide

```
   1   2   3   125      146
[des—Cys—Tyr—Cys,des—Pro— ... —Gln]IFN-γ

(IFN-γ 4-124),
``` and the transformant *Escherichia coli* DH1/pRK248cIts/pLGT-125 (IFO 14649, FERM BP-1476) having the expression plasmid pIGT-125, which encodes the polypeptide

```
   1   2   3   126      146
[des—Cys—Tyr—Cys,des—Ala— ... —Gln]IFN-γ

(IFN-γ 4-125)
``` were obtained, respectively.

EXAMPLE 2

(Culturing of the transformant)

The transformants obtained in Example 1, *Escherichia coli* DH1/pRK248cIts/pIGT-123 (IFO 14647, FERM BP-1474), *Escherichia coli* DH1/pRK248cIts/pIGT-124 (IFO 14648, FERM BP-1475) and *Escherichia coli* DH1/pRK248cIts/pIGT-125 (IFO 14649, FERM BP-1476), were cultured at 30° C. for one night in a 2×TY medium containing 50 μg/ml ampicillin, 1.6% Bacto-Tripton, 1% yeast extract and 0.5% NaCl to obtain a saturated culture liquid, which were then diluted with a 2×TY medium to a 3-fold volume and cultured at 42° C. for 5 hours, after which bacterial cells were separated by centrifugation. These cells were stored at −80° C. under frozen conditions until used.

EXAMPLE 3

(Purification of the polypeptide)

50 g of frozen bacterial cells obtained using the procedure shown in Example 2 were suspended in 48 ml of a sodium borate buffer solution (pH 7.2) containing 7M guanidine hydrochloride and stirred at 4° C. for 1 hour; the suspension was then centrifuged at 22,000×G for 30 minutes to yield 57 ml supernatant, respectively. These supernatants were diluted to a 14-fold volume with a buffer solution composed of 137 mM sodium chloride, 2.7 mM potassium chloride, 8.1 mM disodium phosphate and 1.5 mM monopotassium phosphate (pH 7.4; hereinafter abbreviated PBS) supplemented with 1M urea and passed through an antibody column (Japanese Patent Laid-open No. 107569/1985) [using the monoclonal antibody WNγ2-76.53 (Hybridoma, 6(2), 173 (1987)), 14 ml capacity] at a flow rate of 40 ml/hr. The columns were then washed with 50 ml PBS supplemented with 1M urea and eluted with a 20 mM sodium phosphate buffer solution containing 2M guanidine hydrochloride (pH 7.0) to obtain 37 ml of a fraction containing IFN-γ 4-123, IFN-γ 4-124 and IFN-γ 4-125, respectively.

These fractions were then passed through a column (5.0×51 cm, 1,000 ml capacity) packed with Sephacryl S-200 (Pharmacia) previously equilibrated with a 25 mM ammonium acetate buffer solution (pH 6.0) supplemented with 2M guanidine hydrochloride and eluted with the same buffer solution to obtain 37 ml of a fraction containing IFN-γ 4-123, IFN-γ 4-124 and IFN-γ 4-125, respectively.

These fractions were then dialyzed with 2 l of a 25 mM ammonium acetate buffer solution (pH 6.0) at 4° C.

for 1 day, after which they were dialyzed for 1 more day with an external dialysis liquid renewed. The resulting dialyzates were concentrated using a YM-5 membrane and Diaflo (Amicon, Inc.) and passed through an Acrodisc filter to obtain 5.3 ml filtrate to be used as test samples. Using bovine serum albumin as standard liquid, determinations were made of the protein concentration and total protein content of these sample in accordance with Lowry's method [Lowry et al.; J. Biol. Chem., 193, 265 (1951)]; the figures obtained were respectively 7.9 mg of IFN-γ 4-123, 16.7 mg of IFN-γ 4-124 and 15.6 mg of IFN-γ 4-125 for total protein content.

Figure 3:
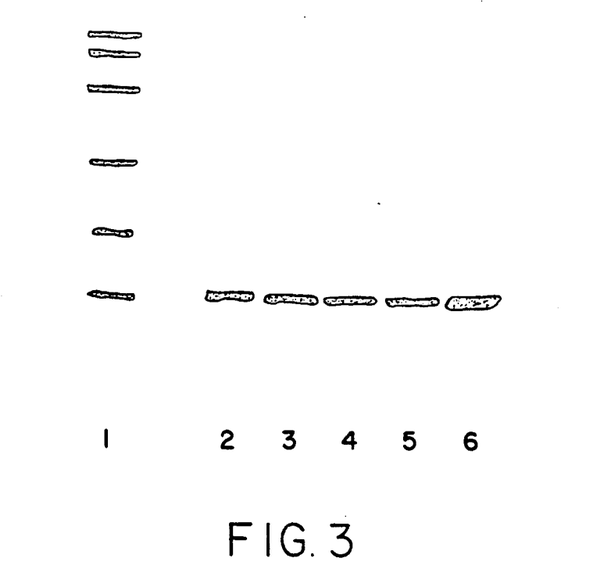
FIG. 3 shows the SDS-PAGE patterns obtained in Example 3 and Reference Example 3.

These samples were analyzed by sodium dodecylsulfate-polyacrylamide gel electrophoresis in accordance with Laemmli's method [Nature, 227, 680 (1970)]. As a result, a single band appeared respectively at the position corresponding to about 14,000 molecular weight (see FIG. 3). In FIG. 3, Patterns 1, 2, 3, 4, 5 and 6 respectively show the results of SDS-PAGE of phosphorylase B (m.w. 92,500)/bovine serum albumin (66,200)/ovalbumin (45,000)/carbonic anhydrase (31,000)/soybean trypsin inhibitor (21,500)/lysozyme (14,400), the polypeptide (hereinafter also referred to as IFN-γ 4-127) obtained by the following Reference Examples, the polypeptide (hereinafter also referred to as IFN-γ 4-126) obtained by the following Reference Example, IFN-γ 4-125, IFN-γ 4-124 and IFN-γ 4-123.

Uniform standard samples of IFN-γ 4-123, IFN-γ 4-124 and IFN-γ 4-125 were obtained, respectively. These standard samples were studied for the following items:

(a) Amino acid composition

70 μg each of the standard samples obtained above was placed in a glass test tube for hydrolysis, and constant boiling point hydrochloric acid was added. After sealing the test tube under reduced pressure, hydrolysis was carried out at 110° C. for 24 hours. After the completion of hydrolysis, the test tube was unsealed, and hydrochloric acid was removed under reduced pressure. The residue was dissolved in 0.02N hydrochloric acid and subjected to amino acid analysis using a Hitachi835-model amino acid analyzer. The results are shown in Table 2.

TABLE 2

| Amino Acid(s) | Number of Residues in Each Molecule* | | |
|---|---|---|---|
| | IFN-γ 4-123 | IFN-γ 4-124 | IFN-γ 4-125 |
| Asp/Asn | 20 | 20 | 20 |
| Thr | 3.9 | 3.8 | 3.7 |
| Ser | 6.6 | 7.2 | 6.8 |
| Glu/Gln | 17.3 | 17.2 | 17.3 |
| Pro | 1.0 | 1.0 | 2.1 |
| Gly | 3.2 | 3.2 | 3.2 |
| Ala | 5.2 | 5.2 | 5.3 |
| Val | 7.3 | 7.5 | 7.6 |
| Met | 3.8 | 3.8 | 3.9 |
| Ile | 6.5 | 6.5 | 6.6 |
| Leu | 9.4 | 9.5 | 9.5 |
| Tyr | 4.0 | 4.1 | 4.1 |

TABLE 2-continued

| Amino Acid(s) | Number of Residues in Each Molecule* | | |
|---|---|---|---|
| | IFN-γ 4-123 | IFN-γ 4-124 | IFN-γ 4-125 |
| Phe | 9.2 | 9.3 | 9.2 |
| Lys | 16.6 | 17.0 | 17.1 |
| His | 1.8 | 1.8 | 1.9 |
| Arg | 3.1 | 3.1 | 3.2 |
| Trp | —** | — | — |

*Calculated on the basis of the number of Asp/Asn residues (=20).
**undetected (b) N-terminal amino acid sequence 12 μg each of the standard samples was analyzed for N-terminal amino acid sequence according to the method of Edman using a gas-phase protein sequencer (470-A model, Applied Biosystems, USA). The identification of phenylthiohidantoin amino acids (PTH-amino acid) was achieved via high performance liquid chromatography using the Micropack SP-ODS column (Varian, Inc., USA). Table 3 lists the detected PTH-amino acids for each step.

TABLE 3

| Step | PTH-amino Acid Detected | | |
|---|---|---|---|
| | IFN-γ 4-123 | IFN-γ 4-124 | IFN-γ 4-125 |
| 1 | Met | Met | Met |
| 2 | Gln | Gln | Gln |
| 3 | Asp | Asp | Asp |
| 4 | Pro | Pro | Pro |
| 5 | Tyr | Tyr | Tyr |

(c) C-terminal amino acid

220 μg each of the standard samples was placed in a glass test tube for hydrazine decomposition, and 0.05 ml anhydrous hydrazine was added. After sealing under reduced pressure, the test tube was heated at 100° C. for 6 hours. The resulting hydrazine decomposition product was lyophilized and dissolved in distilled water. After adding benzaldehyde, this solution was stirred at room temperature for 1 hour and then centrifuged to obtain a supernatant. The resulting supernatant was lyophilized and subjected to amino acid analysis using a Hitachi 835-model amino acid analyzer. As a result, leucine alone, serine alone and proline alone were respectively detected for IFN-γ4-123, IFN-γ4-124 and IFN-γ4-125.

(d) Antiviral activity

IFN-γ4-123, IFN-γ4-124 and IFN-γ4-125 were found to possess an antiviral activity of $14.5 \times 10^6$ U/mg protein, $9.87 \times 10^6$ U/mg protein and $12.1 \times 10^6$ U/mg protein, respectively.

As compared IFN-γ4-123, IFN-γ4-124 and IFN-γ4-125 of the present invention with the polypeptide (hereinafter also referred to as IFN-γ4-121), IFN-γ4-126 and IFN-γ4-127 obtained by the following reference examples, Table 4 lists their antiviral activities.

Table 4

| IFN-γ 4-123 | $14.5 \times 10^6$ U/mg |
|---|---|

| | |
|---|---|
| IFN-γ 4-124 | 9.87 × 10⁶ U/mg |
| IFN-γ 4-125 | 12.1 × 10⁶ U/mg |
| IFN-γ 4-121 | —* |
| IFN-γ 4-126 | 3.3 × 10⁶ U/mg |
| IFN-γ 4-127 | 2.6 × 10⁶ U/mg |

*undetected

As is clear from Table 4, IFN-γ4-123, IFN-γ4-124 and IFN-γ4-125 of the present invention show remarkable antiviral activites.

REFERENCE EXAMPLE 1

Production of transformant

The single-stranded DNA sequence mp 19-IGT (−) obtained by Example 1 and the oligonucleotide (d) synthesized using the amidite phosphate method:

(d) GTCGCCAGCATAGAAAACAGG were used in combination to induce site-specific mutation [Zoller et al.; Methods in Enzymology, 100, 468 (1983)] in the following procedure.

The single-stranded DNA sequence and the synthetic oligonucleotide (d) were reacted with each other to form a double strand. The resulting double strand was then linked to a DNA polymerase Klenow fragment using DNA ligase to prepare a double-stranded closed circular DNA segment. The resulting DNA segment was digested using the restriction enzyme EcoRI to separate a DNA fragment containing a variant plus chain of IFN-γ gene, which was then inserted downstream the λPL promoter in the plasmid pLC2, previously digested using the restriction enzyme EcoRI. Separately, Escherichia coli strain DH1 was transformed using the plasmid pRK248cIts [Hansurich et al.; Methods in Enzymology, 68, 482 (1979)], which has a temperature-sensitive repressor gene of PL promoter, according to the protocol of Maniatis et al. [Molecular Cloning, Cold Spring Harbor Laboratory 1982], to establish the strain E. coli DH1/pRK248cIts. This strain was further transformed using the above-mentioned DNA in the same manner as above.

Out of the resulting transformant colonies, the strain expressing the polypeptide was selected.

The IFN-γ-encoding site of the plasmid contained in this strain was found to be the base sequence as expressed by Formula (II) wherein Y' and Z' respectively represent CAG and (5') GCT GAA CTG TCG CCA GCA (3'), i.e., the desired expression plasmid pIGT-126 was constructed, which encodes the polypeptide Using this plamid, Escherichia coli strain N4830 [Reed; Cell, 25, 713 (1981)] was transformed to obtain the transformant Escherichia coli N4830/pIGT-126 (IFO 14557, FERM P-9113).

REFERENCE EXAMPLE 2

Production of transformant

The single-stranded DNA sequence mp19-IGT(−) obtained by Example 1 and the oligonucleotides (e)-(f) synthesized using the amidite phosphate method; (e) CAAGTGATGGCTTAA TGGTTGTCC or (f) TCGCCAGCAGCTTAATGGTTGTCC were used in combination to obtain the transformant Escherichia coli DH1/pRK248cIes/pIGT-121 having the expression plasmid pIGT-121, which encodes the polypeptide and the transformant Escherichia coli DH1/pRK248cIts/pIGT-127 having the expression plasmid pIGT-127, which encodes the polypeptide respectively, by the same procedure as described in Example 1.

REFERENCE EXAMPLE 3

Culturing of the transformant and purification of the polypeptide

The transformants Escherichia coli DH1/pRK248cIts/pIGT-121, Escherichia coli DH1/pRK248cIts/pIGT-127 and Escherichia coli N4830/pIGT-126 (IFO 14557, FERM P-9113) obtained by Reference Examples 1-2 were respectively cultured by the same procedure as described in Example 2 and bacterial cells were respectively separated by centrifugation. From these cells, samples each of the polypeptide the polypeptide and the polypeptide was obtained by the same purification procedure as described in Example 3.

These samples were respectively analyzed by sodium dodecylsulfate-polyacrylamide gel electrophoresis (SDS-PAGE) in accordance with the description of Example 3. As a result, each single band of the polypeptide and the polypeptide appeared at the position corresponding to about 14,000 molecular weight (see FIG. 3).

With respect to the polypeptide

[des—Cys—Tyr—Cys,des—Glu— ... —Gln]IFN-γ, a single band was obtained but an antiviral activity was not detected.

Uniform standard samples of the polypeptide (IFN-γ 4-126)

and the polypeptide

IFN-γ (IFN-γ 4-127)

were obtained respectively. These samples were studied for the following items:

(a) Amino acid composition

Amino acid analysis was carried out by the same procedure as described in Example 3. The results are shown in Table 5.

TABLE 5

| | Number of Residues in Each Molecule* | |
|---|---|---|
| Amino Acid(s) | IFN-γ 4-126 | IFN-γ 4-127 |
| Asp/Asn | 20 | 20 |
| Thr | 3.9 | 3.8 |
| Ser | 8.2 | 7.6 |
| Glu/Gln | 17.2 | 16.9 |
| Pro | 2.0 | 2.0 |
| Gly | 3.1 | 3.5 |
| Ala | 6.3 | 7.3 |
| Val | 7.5 | 7.8 |
| Met | 4.0 | 3.7 |
| Ile | 6.6 | 6.0 |
| Leu | 9.3 | 8.8 |
| Tyr | 4.1 | 3.9 |
| Phe | 9.4 | 9.1 |
| Lys | 16.1 | 16.3 |
| His | 1.8 | 1.8 |
| Arg | 3.1 | 3.0 |
| Trp | 0.6 | —** |

*Calculated on the basis of the number of Asp/Asn residues (=20).
**undetected (b) N-terminal amino acid sequence N-terminal amino acid sequence was analyzed by the same procedure as described in Example 3. The results are shown in Table 6.

TABLE 6

| | PTH-amino Acid Detected | |
|---|---|---|
| Step | IFN-γ 4-126 | IFN-γ 4-127 |
| 1 | Met | Met |
| 2 | Gln | Gln |
| 3 | Asp | Asp |
| 4 | Pro | Pro |
| 5 | Tyr | Tyr |

(c) C-terminal amino acid

C-terminal amino acid was identified by the same procedure as described in example 3. As a result, alanine alone was detected for both IFN-γ4-126 and IFN-γ-127.

(d) Antiviral activity

IFN-γ4-126 and IFN-γ4-127 were found to possess an antiviral activity of $3.3 \times 10^6$ U/mg protein and $2.6 \times 10^6$ U/mg protein, respectively.

The following references, which are referred to for their disclosures at various points in this application, are incorporated herein by reference.

EP Patent Publication No. 154316
Messing et al.; Nucleic Acids Research, 9, 309 (1981)
Hansurich et al.; Methods in Enzymology, 68, 482 (1979)
Maniatis et al.; Molecular Cloning, pp 250-251, Spring Harbor Laboratory (1982)
Japanese Patent Laid-open No. 107569/1985
Y. Ichimori et al.; Hybridoma, 6(2), 173 (1987)
Lowry et al.; J. Biol. Chem., 193, 265 (1951)
Laemmli et al.; Nature, 227, 680 (1970)

What is claimed is:

1. A DNA segment which consists essentially of a nucleotide region encoding a polypeptide of the formula (I):

wherein X is Met or absent; Y is Gln or absent when X is Met, and Y is Gln, <Glu or absent when X is absent; and Z is an amino acid or a peptide composed of 1 to 4 amino acid residues starting from the N-terminal in the peptide chain (N) Glu Leu Ser Pro (C).

2. The DNA according to claim 1, which comprises ATG at the 5' terminal.

3. A cell transformed with a DNA, which DNA contains a DNA segment consisting essentially of a nucleotide region encoding a polypeptide of the formula (I):

Ala—Z—OH (C)

wherein X is Met or absent; Y is Gln or absent when X is Met, and Y is Gln, <Glu or absent when X is absent; and Z is an amino acid or a peptide composed of 1 to 4 amino acid residues starting from the N-terminal in the peptide chain (N) Glu Leu Ser Pro (C).

4. A plasmid containing a DNA segment which consists essentially of a nucleotide region encoding a polypeptide of the formula (I):

(N) H—X—Y—Asp Pro Tyr Val
Lys Glu Ala Glu Asn Leu Lys
Lys Tyr Phe Asn Ala Gly His
Ser Asp Val Ala Asp Asn Gly
Thr Leu Phe Leu Gly Ile Leu
Lys Asn Trp Lys Glu Glu Ser
Asp Arg Lys Ile Met Gln Ser
Gln Ile Val Ser Phe Tyr Phe
Lys Leu Phe Lys Asn Phe Lys
Asp Asp Gln Ser Ile Gln Lys
Ser Val Glu Thr Ile Lys Glu
Asp Met Asn Val Lys Phe Phe
Asn Ser Asn Lys Lys Lys Arg
Asp Asp Phe Glu Lys Leu Thr
Asn Tyr Ser Val Thr Asp Leu
Asn Val Gln Arg Lys Ala Ile
His Glu Leu Ile Gln Val Met
Ala—Z—OH (C)

wherein X is Met or absent; Y is Gln or absent when X is Met, and Y is Gln, <Glu or absent when X is absent; and Z is an amino acid or a peptide composed of 1 to 4 amino acid residues starting from the N-terminal in the peptide chain (N) Glu Leu Ser Pro (C).

* * * * *